US008088409B2

(12) United States Patent
Friesen et al.

(10) Patent No.: US 8,088,409 B2
(45) Date of Patent: Jan. 3, 2012

(54) COMPOSITIONS AND METHODS FOR IMPROVING SKIN HEALTH AND PELAGE QUALITY

(75) Inventors: Kim Gene Friesen, Topeka, KS (US); Ryan Michael Yamka, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 137 days.

(21) Appl. No.: 11/558,730

(22) Filed: Nov. 10, 2006

(65) Prior Publication Data

US 2007/0196505 A1 Aug. 23, 2007

Related U.S. Application Data

(60) Provisional application No. 60/735,904, filed on Nov. 10, 2005.

(51) Int. Cl.
*A23K 1/17* (2006.01)
(52) U.S. Cl. .................. 424/442; 514/560
(58) Field of Classification Search .................. None
See application file for complete search history.

(56) References Cited

U.S. PATENT DOCUMENTS

| 5,756,088 A | 5/1998 | Matsuura et al. |
| 6,737,078 B1 | 5/2004 | Kelley |
| 2005/0032897 A1 | 2/2005 | Kelley |
| 2006/0045909 A1* | 3/2006 | Friesen et al. .................. 424/442 |

FOREIGN PATENT DOCUMENTS

| EP | 0 678 247 | 10/1995 |
| FR | 2 878 744 | 6/2006 |
| WO | WO 02/07531 A1 | 1/2002 |
| WO | WO 03/092405 A2 | 11/2003 |
| WO | WO 2005/051093 A1 | 6/2005 |

OTHER PUBLICATIONS

Wander et al. , Journal of Nutrition, 1997, vol. 127, p. 1198-1205.*
Watson et al., Journal of Nutrition, 1998, vol. 128, 2783S-2789S.*
Ahlstrom et al., Journal of Nutrition, Aug. 2004, vol. 134, 2145S-2147S.*
Heinmann et al. , Journal of Nutrition, Aug. 2005, vol. 135, p. 1960-1966.*
Wynn et al., Clinical Techniques in Small Animal Practice, 2002, vol. 17, No. 1, p. 37-40.*
Olivry et al., Veterinary Immunology and Immunopathology, 2001, vol. 81, p. 347-362.*
Wander et al., Journal of Nutrition, 1997, vol. 127, p. 1198-1205.*
Byrne et al., Veterinary Dermatology, 2000, vol. 11, p. 123-131.*
2005 Official Publication of American Feed Control Officials, pp. 131-140.
Small Animal Nutrition, 2000, pp. 127-146.
"The Effect of the Addition of Oil Preparation with Increased Content of N-3 Fatty Acids on Serum Lipid Profile and Clinical Condition of Cats with Miliary Dermmatitis"; by Lechowski et al .; *Journal of Veterinary Medicine*; vol. 45, No. 6/7; 1998; pp. 417-424. XP000971544.
"Effects of Dietary N-6 and N-3 Fatty Acids and Vitamin E on the Immune Response of Healthy Geriatric Dogs"; by Hall et al .; *American Journal of Veterinary Research*; vol. 64, No. 6; 2003; pp. 762-772. XP008076205.
"The Ratio of Dietary (N-6) to (N-3) Fatty Acids Influences Immune System Function, Eicosanoid Metabolism, Lipid Peroxidation and Vitamin E Status in Aged Dogs 1-4"; by Wander et al .; *American Society of Nutritional Sciences*; vol. 127, No. 6; 1997; pp. 1198-1205. XP000978825.
"The Intake of Polyunsaturated Fatty Acids by Cats is Reflected in Their Adipose Tissue"; by Neil et al. ; *Veterinary Quarterly*; vol. 19, No. 4; Nov. 1997; pp. 150-153. XP001024197.
"The Return of Omega-3 Fatty Acids Into the Food Supply. I. Land Based Animal Food Products and Their Health Effects"; by Simopoulos et al .; *World Review of Nutrition and Dietetics*; vol. 83, 1998; pp. 176-175. XP002172305.
"Dietary N-3 and N-6 Fatty Acids Effects on Canine Bone and Ligament Composition"; by Rogers et al .; *Faseb Journal, Fed of American Soc. for Experimental Biology*; vol. 14, No. 4; Mar. 15, 2000; p. a252. XP002172303.
"Varying the Ratio of Dietary N-6/N-3 Polyunsaturated Fatty Acids Alters the Tendencey to Thrombosis and Progress of Artherosclerosis in ApoE<−/−>LDLR <−/−> Double Knockout Mouse"; by Yamashita et al .; *Thrombosis Research*; vol. 116, No. 5; Feb. 25, 2005; pp. 393-401. XPXP005040792.
"Effects of Different Ratios of Dietary N-6 and N-3 Fatty Acids on Fatty Acid Composition, Prostaglandin Formation and Platelet Aggregation in the Rat"; by Takahashi et al .; *Thombosis Research*; vol. 47, No. 21987; pp. 135-146. XP 002907576.
"Arachidonic Acid Offsets the Effects on Mouse Brain and Behavior of a Diet with a Low (N-6): (N-3) Ratio and Very High Levels of Docosahexaenoic Acid", by Wainright et al .; *Journal of Nutrition*; vol. 127; 1997; pp. 184-193.
"Effect of Age, Breed and Dietary Omega-6 (N-6): Omega-3 (N-3) Fatty Acid Ration on Immune Function, Eicosanoid Production, and Lipid Peroxidation in Young and Aged Dogs"; by Kearns et al .; *Veterinary Immunology and Immunopathology*; vol. 69, No. 2/4; 1999; pp. 165-183. XP000924834.

* cited by examiner

*Primary Examiner* — Kade Ariani
(74) *Attorney, Agent, or Firm* — Shannon McGarrah

(57) ABSTRACT

Compositions and methods for improving animal skin health and/or pelage quality that utilize one or more omega-6 fatty acids and one or more omega-3 fatty acids at a total omega-6 to total omega-3 fatty acid ratio of from about 1 to less than 5.

16 Claims, No Drawings

COMPOSITIONS AND METHODS FOR IMPROVING SKIN HEALTH AND PELAGE QUALITY

CROSS-REFERENCE TO RELATED APPLICATION

This application claims priority to U.S. Provisional Application Ser. No. 60/735,904 filed Nov. 10, 2005, the disclosure of which is incorporated herein by reference.

BACKGROUND OF THE INVENTION

1. Field of the Invention

The present invention relates generally to compositions for improving animal skin health and/or pelage quality. The invention also relates generally to methods for preparing such compositions, methods for using such compositions, articles of manufacture comprising such compositions, and means for communicating information about such compositions, methods, and articles of manufacture.

2. Description of the Relevant Art

Skin is the largest and most visible organ of the body and the anatomic and physiologic barrier between animal and environment. It provides protection from physical, chemical, and microbiologic injury, and its sensory components perceive heat, cold, pain, pruritus, touch, and pressure. Pelage is the hair, fur, or wool that covers an animal. Pelage is sometimes referred to as an animal's coat. Skin and pelage vary in quantity and quality among species, and among individuals within a species. Skin and pelage also vary from one area to another on the body and in accordance with age and sex.

Pelage is important in thermal insulation and sensory perception and as a barrier against chemical, physical, and microbial injury to the skin. Also, pelage is photoprotective. The pelage's ability to regulate body temperature correlates closely with its length, thickness, and density per unit area, and with the medullation of individual pelage fibers. Coat color also has some importance in thermal regulation, with light-colored coats being more efficient in hot, sunny weather. The glossiness of the pelage is important in reflecting sunlight.

Pelage such as hair does not grow continuously but rather in cycles, with each cycle consisting of a growing period (anagen), during which the follicle is actively producing hair, and a resting period (telogen), during which the hair is retained in the follicle as a dead hair that is subsequently lost. There is also a transitional period (catagen) between these two stages. The relative duration of the phases of the cycle varies with age, breed, sex, and the region of the body, and can be modified by a variety of physiologic and pathologic factors. The hair cycle, and thus the coat, are controlled by photoperiod, ambient temperature, nutrition, hormones, general state of health, genetics, and intrinsic factors such as, for example, growth factors and cytokines produced by the follicle, the dermal papilla, and other cells in the immediate environment (e.g., lymphocytes, macrophages, fibroblasts, and mast cells).

Because pelage is predominantly made of protein, nutrition has a profound effect on its quantity and quality. Poor nutrition may produce dull, dry, brittle, or thin pelage with or without pigmentary disturbances. Under conditions of ill health or generalized disease, anagen may be considerably shortened and a large percentage of body hairs may be in telogen at one time. Because telogen hairs tend to be more easily lost, the animal may shed excessively. Diseases may also lead to faulty formation of hair cuticle, which results in a dull, lusterless pelage. Severe illness or systemic stress may cause many hair follicles to enter synchronously and precipitously into telogen. Shedding of these hairs thus occurs simultaneously, often resulting in visible thinning of the coat or actual alopecia.

Because skin and pelage are important for an animals' health, there is a need for alternative compositions and methods for improving animal skin health and/or pelage quality.

SUMMARY OF THE INVENTION

It is an object of the present invention to provide compositions for improving animal skin health and/or pelage quality.

It is another object of the invention to provide methods for improving animal skin health and/or pelage quality.

It is another object of the invention to provide articles of manufacture comprising a composition of the invention and, optionally, one or more agents for improving animal skin health, improving animal pelage quality, and/or promoting animal health or wellness.

It is a further object of the invention to provide articles of manufacture comprising two or more ingredients that, when combined together and optionally with additional ingredients that are not a part of the article of manufacture, yield a composition of the invention. The articles of manufacture may optionally comprise one or more agents for improving skin health, improving pelage quality, and/or promoting the health or wellness of animals.

It is another object of the invention to provide means for communicating information about the compositions, methods, and articles of manufacture of the invention.

These and other objects are achieved using novel compositions that comprise one or more omega-6 fatty acids and one or more omega-3 fatty acids and that have a total omega-6 to total omega-3 fatty acid ratio of from about 1 to less than 5. Such compositions are surprisingly effective for improving animal skin health and/or pelage quality.

Additional objects, features, and advantages of the invention will be apparent to those skilled in the art from reading this patent.

DETAILED DESCRIPTION OF THE INVENTION

In one aspect, the present invention provides a composition for improving animal skin health and/or pelage quality. The composition is suitable for growing, adult, senior, and geriatric animals. A growing animal is one that has not reached adult size. An adult animal is one of any age after the completion of juvenile growth and development, including senior and geriatric animals. For example, for cats and dogs this typically means an age of about 1 year through the remainder of their life. A senior animal is one of an age having an increased risk for age-related disease which may but need not have obvious physical or behavioral characteristics of aging. Typically, but depending on breed, a senior dog is one of about 7 through about 9 years of age, a senior large breed dog is one of about 5 years of age and beyond, and a senior cat is one of about 7 through about 11 years of age. A geriatric animal is one showing outward signs of aging, typically, for example, a dog of about 10 years of age and beyond, a large breed dog of about 7 years of age and beyond, or a cat of about 12 years of age and beyond. In some embodiments, the animal is a member of the order Carnivora. In some such embodiments, the animal is a canine, and in other such embodiments the animal is a feline. In some embodiments, the animal is a companion animal. A companion animal can be, for example, an animal of any species that is kept as a pet. A companion animal can also be an animal from a variety of widely domesticated species, for example, dogs (*Canis familiaris*) and cats (*Felis domesticus*) regardless of whether or not the animal is kept solely as a pet. Thus, companion animals include, for example, working dogs and pet cats and dogs. The term "animal" as used herein means an animal that has skin and/or pelage.

The composition comprises one or more omega-6 fatty acids and one or more omega-3 fatty acids in a total omega-6 to total omega-3 fatty acid ratio of from about 1 to less than 5. Fatty acids are long carbon chains with a methyl group at one end. Polyunsaturated fatty acids have multiple double bonds. The fatty acids that have the first double bond three carbons away from the methyl group are the omega-3 (or n-3) series. The omega-6 (or n-6) series of polyunsaturated fatty acids have the first double bond six carbons from the methyl group. In mammals, polyunsaturated omega-3 and omega-6 fatty acids are essential fatty acids ("EFAs") because they cannot be synthesized de novo by mammals. Members of the omega-6 family include, for example, linoleic (18:2n-6), gamma-linolenic (18:3n-6), dihomogammalinolenic (20:3n-6), and arachidonic acid (20:4n-6). Members of the omega-3 family include, for example, alpha-linolenic (18:3n-3), elcosatetraenoic (20:4n-3), eicosapentaenoic (20:5n-3), and docosahexaenoic acid (22:6n-3). In the skin, EFAs are principally found in phospliolipids. The high degree of unsaturation of EFAs bestows fluidity to phospholipids at physiologic temperatures, allowing conformational changes to occur. One of the skin-related functions of EFAs is the incorporation of linoleic acid into the ceramides of the lipid portion of the epidermal cornified envelope. This envelope serves a barrier function to prevent loss of water and other nutrients. EFAs are a source of energy for the skin and serve as precursors to a variety of potent, short-lived molecules including prostaglandins, leukotrienes, and their metabolites. In some embodiments, the composition comprises an amount of linoleic acid that is equal to or higher than the minimum allowance recommended by the Association of American Feed Control Officials ("AAFCO"). In some embodiments, the composition comprises an amount of linoleic acid that is up to about 200% higher, up to about 300% higher, up to about 400% higher, up to about 500% higher, up to about 600% higher, up to about 700% higher, up to about 800% higher, up to about 900% higher, up to about 1000% higher, or up to about 100% higher than the respective AAFCO minimum allowance. The AAFCO's minimum linoleic acid allowance for growth, reproduction, and maintenance of dogs is 1% on a dry matter basis (presuming that the energy density of the diet is 3.5 kcal ME/g dry matter). The AAFCO's minimum linoleic acid allowance for growth, reproduction, and maintenance of cats is 0.5% on a dry matter, respectively (presuming that the energy density of the diet is 4.0 kcal ME/g dry matter). See 2005 Official Publication of Association of American Feed Control Officials.

The total omega-6 to total omega-3 fatty acids ratio of the composition is from about 1 to less than 5. The total omega-6 to total omega-3 fatty acids ratio of a composition is the total amount of the omega-6 fatty acids present in the composition relative to the total amount of the omega-3 fatty acids present in the composition. In some embodiments, the composition has a total omega-6 to total omega-3 fatty acid ratio of from about 1.5 to about 4.5. In other embodiments, the composition has a total omega-6 to total omega-3 fatty acid ratio of from about 2 to about 3.2. In further embodiments, the composition has a total omega-6 to total omega-3 fatty acid ratio of about 4 to about 4.5.

In some embodiments, a composition is such that upon feeding the composition to an animal, the total omega-6 to total omega-3 fatty acid ratio in the animal's blood is of from about 1 to about 5. The total omega-6 to total omega-3 fatty acids ratio of blood is the total amount of the omega-6 fatty acids present in a blood sample obtained from the animal relative to the total amount of the omega-3 fatty acids present in the blood sample. In some such embodiments, the composition is such that upon feeding the composition to an animal, the total omega-6 to total omega-3 fatty acid ratio in the animal's blood is from about 2 to about 4.8. In other such embodiments, the composition is such that upon feeding the composition to an animal, the total omega-6 to total omega-3 fatty acid ratio in the animal's blood is from about 3 to about 4.5. In further Such embodiments, the composition is such that upon feeding the composition to an animal, the total omega-6 to total omega-3 fatty acid ratio in the animal's blood is from about 3.5 to about 4.

In some embodiments, the composition comprises a food composition. In some embodiments, the food composition meets the AAFCO's minimum nutrient level requirements for growth, reproduction, or maintenance depending on the animal's age. In some embodiments, the food composition comprises a dry food (i.e., a food containing from about 3 to about 1% water). In other embodiments, the food composition comprises a semi-moist food (i.e., a food containing from about 25 to about 35% water). In some embodiments, the food composition comprises a moist food (i.e., a food containing from about 60 to more than about 87% water). In some embodiments, the food composition comprises a treat, snack, supplement, or partially or fully edible toy.

A composition of the present invention can be prepared by mixing one or more food compositions and optionally one or more additional ingredients such as, for example, omega-6 and/or omega-3 fatty acids. A composition of the present invention can also be prepared by one or more of the methods discussed in, for example, Small Animal Nutrition, pages 127-46 (2000).

In a further aspect, the present invention provides for a use of a composition comprising one or more omega-6 fatty acids and one or more omega-3 fatty acids in a total omega-6 to total omega-3 fatty acid ratio of from about 1 to less than 5 to prepare a medicament. In another, the invention provides for the use of such composition to prepare a medicament for maintaining and/or improving animal health, e.g., for improving animal skin health and/or pelage quality. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

In another aspect, the present invention provides a method for improving animal skin health and/or pelage quality. The method comprises feeding the animal a composition comprising one or more omega-6 fatty acids and one or more omega-3 fatty acids in a total omega-6 to total omega-3 fatty acid ratio of from about 1 to less than 5. In some embodiments, a single composition of this invention is fed to the animal. In other embodiments, different compositions of this invention are fed to the animal for varying time intervals until the animal reaches adult size.

In some embodiments, the method of the invention further comprises administering to the animal one or more agents for improving skin health, improving pelage quality, and/or promoting the health or wellness of the animal. Health of an animal refers to the absence of disease or infirmity. Wellness refers to the complete physical, mental, and social wellbeing of the animal, not merely the absence of infinity. The term "in conjunction" means that an agent is administered to the animal either together with a composition of the present invention or separately from the composition at the same or different frequency via the same or different administration route and either at about the same time as the composition or periodically. "About at the same time" generally means that an agent is administered to an animal when a composition of the present invention is fed to the animal or within about 72 hours of feeding the composition to the animal. "Periodically" generally means that an agent is administered to an animal following a dosage schedule suitable for administering that agent while a composition of the present invention is fed to the animal routinely as appropriate for that animal. Thus, the term "in conjunction" specifically includes situations when an agent is administered to an animal for a prescribed period of time while a composition of the present invention is fed to the animal until it reaches normal adult size. If two or more agents are to be administered to an animal, the dosage schedule and route of administration for each agent may vary. In addition, as discussed above, one composition of the present invention may be substituted with another composition of the present invention while a specific agent is administered to the animal.

In some embodiments, the agent for improving skin health and/or pelage quality comprises a topical drug. Topical drugs include, for example, astringents, emollients, moisturizers, antipruritics, antiseborrheics, antimicrobials, and anti-inflammatory agents. These drugs may be applied to the skin by a variety of delivery systems, for example, shampoos, rinses, powders, lotions, sprays, creams, emulsions, ointments, and gels. In some embodiments, the agent for promoting health or wellness comprises one or more drugs for treating, for example, a bacterial, fungal, parasitic, or viral skin disease or an immune-mediated, endocrine, or metabolic disease. In some embodiments, the agent for promoting health or wellness comprises one or more antioxidants. In some embodiments, the agent for promoting health or wellness comprises one or more vitamins.

In another aspect, the present invention provides an article of manufacture, such as for example a kit comprising a composition comprising one or more omega-6 fatty acids and one or more omega-3 fatty acids in a total omega-6 to total omega-3 fatty acid ratio of from about 1 to less than 5. In some embodiments, the kit further comprises one or more agents for improving skin health, improving pelage quality, and/or promoting the health or wellness of an animal. In some embodiments, the kit further comprises instructions for at least one of (1) feeding a composition of the present invention to an animal, (2) administering an agent for improving skin health, improving pelage quality, and/or promoting the health or wellness of an animal in conjunction with a composition of the present invention.

In another aspect, the present invention provides an article of manufacture, such as for example a kit comprising two or more ingredients that, when combined together and optionally with additional ingredients that are not a part of the kit, yield a composition comprising one or more omega-6 fatty acids and one or more omega-3 fatty acids in a total omega-6 to total omega-3 fatty acid ratio of from about 1 to less than 5. In some embodiments, the kit further comprises one or more agents for improving skin health, improving pelage quality, and/or promoting the health or wellness of an animal. In some embodiments, the kit further comprises instructions for at least one of (1) making a composition of the present invention by combining the two or more ingredients and, optionally, additional ingredients that are not a part of the kit, (2) feeding the composition to an animal, and (3) administering one or more agents for improving skin health, improving pelage quality, and/or promoting the health or wellness of an animal in conjunction with the composition.

In some embodiments, the kit comprises in separate containers in a single package or in separate containers in a virtual package, as appropriate a composition of the present invention or two or more ingredients, that, when combined together and optionally with additional ingredients that are not a part of the kit, yield a composition comprising one or more omega-6 fatty acids and one or more omega-3 fatty acids in a total omega-6 to total omega-3 fatty acid ratio of from about 1 to less than 5 and at least one of (1) instructions for feeding the composition to an animal, (2) instructions for making a composition of the present invention by combining the two or more ingredients, (3) one or more agents for improving skin health, improving pelage quality, and/or promoting the health or wellness of an animal, and (4) instructions for administering the agents in conjunction with the composition. The term "single package" generally means that the components of a kit are physically associated in or with one or more containers and considered as a unit of manufacture, distribution, sale, or use. Containers include, but are not limited to, bags, boxes, bottles, shrink wrap packages, stapled or otherwise fixed components, or combinations thereof. A single package can be, for example, containers or individual food compositions physically associated such that they are considered a unit for manufacture, distribution, sale, or use. The term "virtual package" generally means that the components of a kit are associated by directions on one or more physical or virtual kit components instructing the user how to obtain additional components, e.g., in a bag containing one component and directions instructing the user to go to a website, contact a recorded message, view a visual message, or contact a caregiver to obtain instructions on how to use the kit. When the kit comprises a virtual package, the kit is limited to instructions in a virtual environment with one or more physical kit components.

In another aspect, the present invention provides a means for communicating information about or instructions for one or more of (1) using a composition of the present invention for improving animal skin health and/or pelage quality, (2) using a composition of the present invention in conjunction with one or more agents for improving skin health, improving pelage quality, and/or promoting the health or wellness of an animal, and (3) using a kit of the present invention for improving animal skin health and/or pelage quality comprising a document, digital storage media, optical storage media, audio presentation, or visual display containing the information or instructions. In certain embodiments, the communicating means comprises a document, digital storage media, optical storage media, audio presentation, or visual display containing the information or instructions. Preferably, the communication means is a displayed web site or a brochure, product label, package insert, advertisement, or visual display containing such information or instructions. Useful information or instructions include, for example, (1) information and instructions how to use a composition, method, or kit of the present invention and (2) contact information for animal caregivers if they have a question about the invention and its uses.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly indicates otherwise. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of this invention. Although any methods and materials similar or equivalent to those described herein can be used in the practice of the present invention, the preferred methods, devices, and materials are described herein.

All references mentioned herein are incorporated herein by reference to the extent allowed by law for the purpose of describing and disclosing the compositions, compounds, methods, and similar information reported herein that might be used in the present invention. However, nothing herein is to be construed as an admission that the invention is not entitled to antedate such disclosure by virtue of prior invention.

EXAMPLES

This invention can be further illustrated by the following examples, although it will be understood that the examples are included merely for purposes of illustration and are not intended to limit the scope of the invention unless otherwise specifically indicated.

Example 1

This example utilized 40 healthy geriatric dogs (10 years or older). The dogs were determined to be healthy by physical exam and blood chemistry screen. All dogs were fed a control food for 30 days. After that, the dogs were split into 4 groups with 10 dogs in each group. The 4 groups were fed one of foods A, B, C, or D for 3 months. All foods met the AAFCO's minimum nutrient allowances for maintenance. The results from the nutrient analysis of the foods are presented in Table 1.

TABLE 1

Nutrient Analysis of Foods A, B, C, and D

| Nutrient | Food A | Food B | Food C | Food D |
|---|---|---|---|---|
| Crude protein, % DMB | 19.3 | 31.4 | 27.8 | 29.4 |
| Fat, % DMB | 17.0 | 16.6 | 11.6 | 13.7 |
| Calcium, % DMB | 0.69 | 0.82 | 1.36 | 1.54 |
| Phosphorus, % DMB | 0.59 | 0.78 | 0.89 | 1.22 |
| Methionine, % DMB | 1.00 | 0.49 | 0.51 | 0.66 |
| Linoleic acid, % DMB | 4.00 | 2.92 | 1.90 | 2.60 |
| EPA, % DMB | 0.32 | 0.10 | <0.01 | 0.10 |
| Total omega-6 fatty acids, % DMB | 3.96 | 3.10 | 1.79 | 2.66 |
| Total omega-3 fatty acids, % DMB | 1.30 | 0.48 | 0.13 | 0.41 |
| Omega-6 to omega-3 ratio | 3.05 | 6.46 | 13.77 | 6.49 |

Blood was drawn from all dogs at days 0, 30, and 90, and the levels of vitamin E, triglyceride, and fatty acids in serum were determined. The levels of these compounds in the blood reflect the availability of these nutrients for the dog's skin and pelage. The results from the blood analysis are presented in Tables 2 and 3, with the total omega-6 to total omega-3 fatty acid ratios for the blood samples presented in the last row of those tables.

TABLE 2

Blood Analysis of Dogs Fed Foods A, B, C, and D at Day 30

| Metabolite | Food A | Food B | Food C | Food D |
|---|---|---|---|---|
| Linoleic acid, mg/dL | 62.3 | 59.3 | 50.3 | 50.2 |
| EPA, mg/dL | 9.80 | 3.96 | 1.53 | 3.68 |
| DHA, mg/dL | 16.6 | 10.0 | 3.9 | 11.7 |
| Total omega-6 fatty acids, mg/dL | 107 | 126 | 104 | 114 |
| Total omega-3 fatty acids, mg/dL | 28.5 | 15.2 | 6.4 | 17.0 |
| Omega-6 to omega-3 ratio | 3.76 | 8.29 | 16.25 | 6.71 |

TABLE 3

Blood Analysis of Dogs Fed Foods A, B, C, and D at Day 90

| Metabolite | Food A | Food B | Food C | Food D |
|---|---|---|---|---|
| Linoleic acid, mg/dL | 62.7 | 60.3 | 55.8 | 53.0 |
| EPA, mg/dL | 9.02 | 3.70 | 1.51 | 3.52 |
| DHA, mg/dL | 17.4 | 12.1 | 3.9 | 14.5 |
| Total omega-6 fatty acids, mg/dL | 108 | 134 | 112 | 124 |
| Total omega-3 fatty acids, mg/dL | 28.9 | 17.7 | 6.9 | 20.0 |
| Omega-6 to omega-3 ratio | 3.74 | 7.57 | 16.23 | 6.2 |

Example 2

This example utilized 40 healthy geriatric cats (12 years old or over). The cats were determined to be healthy by physical exam and blood chemistry screen. All cats were fed a control food for 30 days. After that, the cats were split into 4 groups with 10 cats in each group. The 4 groups were fed one of foods E, F, G, or H for 3 months. All foods met the AAFCO's minimum nutrient allowances for maintenance. The results from the nutrient analysis of the foods are presented in Table 4.

TABLE 4

Nutrient Analysis of Foods E, F, G, and H

| Nutrient | Food E | Food F | Food G | Food H |
|---|---|---|---|---|
| Crude protein, % DMB | 35.73 | 34.85 | 30.52 | 40.45 |
| Fat, % DMB | 22.47 | 15.39 | 23.63 | 15.69 |
| Calcium, % DMB | 0.94 | 1.22 | 0.80 | 1.38 |
| Phosphorus, % DMB | 0.77 | 1.05 | 0.72 | 1.30 |
| Methionine, % DMB | 1.32 | 1.05 | 0.72 | 0.77 |
| Linoleic acid, % DMB | 5.05 | 2.78 | 4.78 | 2.17 |
| EPA, % DMB | 0.32 | 0.07 | 0.13 | 0.07 |
| DHA, % DMB | 0.23 | 0.08 | 0.11 | 0.07 |
| Total n-6 fatty acids, % DMB | 5.09 | 2.87 | 5.02 | 2.13 |
| Total n-3 fatty acids, % DMB | 1.14 | 0.28 | 0.74 | 0.32 |
| Omega-6 to omega-3 ratio | 4.46 | 10.25 | 6.75 | 6.65 |

Blood was drawn from all cats at days 0, 30, and 90, and the levels of vitamin E, triglyceride, and fatty acids in serum were determined. The levels of these compounds in the blood reflect the availability of these nutrients for the cat's skin and pelage. The results from the blood analysis are presented in Tables 5 and 6, with the total omega-6 to total omega-3 fatty acid ratios for the blood samples presented in the last row of those tables.

TABLE 5

Blood Analysis of Cats Fed Foods E, F, G, and H at Day 30

| Metabolite | Food E | Food F | Food G | Food H |
|---|---|---|---|---|
| Linoleic acid, mg/dL | 41.8 | 34.7 | 48.6 | 31.5 |
| EPA, mg/dL | 5.3 | 1.5 | 3.4 | 2.3 |
| DHA, mg/dL | 6.1 | 4.2 | 3.7 | 4.4 |
| Total omega-6 fatty acids, mg/dL | 56.3 | 55.5 | 68.1 | 47.1 |
| Total omega-3 fatty acids, mg/dL | 12.5 | 6.3 | 8.2 | 7.4 |
| Omega-6 to omega-3 ratio | 4.50 | 8.81 | 8.30 | 6.36 |

TABLE 6

Blood Analysis of Cats Fed Foods E, F, G, and H at Day 90

| Metabolite | Food E | Food F | Food G | Food H |
|---|---|---|---|---|
| Linoleic acid, mg/dL | 36.2 | 33.3 | 46.3 | 27.6 |
| EPA, mg/dL | 5.4 | 1.9 | 3.5 | 2.8 |
| DHA, mg/dL | 6.5 | 4.7 | 4.4 | 5.1 |
| Total omega-6 fatty acids, mg/dL | 50.1 | 54.2 | 65.5 | 43.6 |
| Total omega-3 fatty acids, mg/dL | 13.0 | 7.3 | 9.1 | 8.7 |
| Omega-6 to omega-3 ratio | 3.85 | 7.42 | 7.20 | 5.01 |

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the invention are possible in light of the above teachings. It is therefore to be understood that within the scope of the appended claims the invention may be practiced otherwise than as specifically described.

What is claimed is:

1. A method for improving animal skin health and/or pelage quality in a growing animal comprising feeding the animal a food composition that comprises linoleic acid in an amount of at least 4% by weight on a dry matter basis and optionally one or more additional omega-6 fatty acid, eicosapentaenoic acid in an amount of at least 0.3% by weight on a dry matter basis and optionally one or more omega-3 fatty acid, wherein said composition has a total omega-6 to total omega-3 fatty acid ratio of from about 1.5 to 4.5, and wherein said composition further comprises one or more antioxidant and one or more vitamin.

2. The method of claim 1 wherein the composition has a total omega-6 to total omega-3 fatty acid ratio of from about 2 to about 3.2.

3. The method of claim 1 wherein, upon feeding the composition, the total omega-6 to omega-3 fatty acid ratio in the animal's blood is from about 1 to about 5.

4. The method of claim 1 wherein, upon feeding the composition, the total omega-6 to total omega-3 fatty acid ratio in the animal's blood is from about 3 to about 4.5.

5. The method of claim 1 wherein the method further comprises administering to the animal one or more agents for improving skin health, improving pelage quality.

6. The method of claim 1 wherein the animal is a companion animal.

7. The method of claim 1 wherein the animal is a canine.

8. The method of claim 1 wherein the animal is a feline.

9. A method for improving animal skin health and/or pelage quality in a growing animal comprising feeding the animal a food composition that comprises linoleic acid in an amount of at least 4% by weight on a dry matter basis and optionally one or more additional omega-6 fatty acid, and further comprises omega-3 fatty acids in a total amount of at least 1.3% by weight on a dry matter basis, wherein said composition has a total omega-6 to total omega-3 fatty acid ratio of from about 1.5 to 4.5, and wherein said composition further comprises one or more antioxidant and one or more vitamin.

10. The method as in claim 9 wherein the composition has a total omega-6 to total omega-3 fatty acid ratio of from about 2 to about 3.2.

11. The method as in claim 9 wherein, upon feeding the composition, the total omega-6 to omega-3 fatty acid ratio in the animal's blood is from about 1 to about 5.

12. The method as in claim 9 wherein, upon feeding the composition, the total omega-6 to total omega-3 fatty acid ratio in the animal's blood is from about 3 to about 4.5.

13. The method as in claim 9 wherein the method further comprises administering to the animal one or more agents for improving skin health, improving pelage quality.

14. The method as in claim 9 wherein the animal is a companion animal.

15. The method as in claim 9 wherein the animal is a canine.

16. The method as in claim 9 wherein the animal is a feline.

* * * * *